(12) United States Patent
Nau, Jr.

(10) Patent No.: US 8,652,135 B2
(45) Date of Patent: Feb. 18, 2014

(54) SURGICAL FORCEPS

(75) Inventor: William H. Nau, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 792 days.

(21) Appl. No.: 12/861,209

(22) Filed: Aug. 23, 2010

(65) Prior Publication Data

US 2012/0046660 A1 Feb. 23, 2012

(51) Int. Cl.
*A61B 18/14* (2006.01)

(52) U.S. Cl.
USPC .......................................... 606/51; 606/207

(58) Field of Classification Search
USPC ................. 606/41, 45–52, 180, 205–207
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,456,689 A | 10/1995 | Kresch et al. |
| 5,509,923 A | 4/1996 | Middleman et al. |
| 5,540,706 A | 7/1996 | Aust et al. |
| 5,569,284 A * | 10/1996 | Young et al. .................. 606/180 |
| D384,413 S | 9/1997 | Zlock et al. |
| 5,810,805 A * | 9/1998 | Sutcu et al. ..................... 606/45 |
| D402,028 S | 12/1998 | Grimm et al. |
| D416,089 S | 11/1999 | Barton et al. |
| 6,017,340 A | 1/2000 | Cassidy et al. |
| D424,694 S | 5/2000 | Tetzlaff et al. |
| D425,201 S | 5/2000 | Tetzlaff et al. |
| D449,886 S | 10/2001 | Tetzlaff et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley

(57) ABSTRACT

A forceps includes a housing having a shaft attached thereto and an end effector assembly disposed at a distal end of the shaft. The end effector assembly includes first and second jaw members disposed in opposed relation relative to one another. At least one of the jaws is moveable with respect to the other between a spaced-apart position and an approximated position for grasping tissue between the jaw members. A cutting assembly is disposed within a cavity defined within the first jaw member. The cutting assembly includes a cutting member that is rotatably coupled to the first jaw member and configured to rotate with respect to the first jaw member about a longitudinal axis thereof to cut tissue disposed between the jaw members.

11 Claims, 3 Drawing Sheets

(56) References Cited

U.S. PATENT DOCUMENTS

| | | |
|---|---|---|
| D454,951 S | 3/2002 | Bon |
| D457,958 S | 5/2002 | Dycus et al. |
| D457,959 S | 5/2002 | Tetzlaff et al. |
| 6,398,741 B2 | 6/2002 | Niizeki et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,860,880 B2 | 3/2005 | Treat et al. |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 8,100,906 B2* | 1/2012 | Hafner .................. 606/51 |
| 2003/0018332 A1 | 1/2003 | Schmaltz et al. |
| 2004/0102804 A1 | 5/2004 | Chin |
| 2006/0167450 A1* | 7/2006 | Johnson et al. .......... 606/48 |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0249769 A1 | 9/2010 | Nau, Jr. et al. |
| 2010/0249776 A1 | 9/2010 | Kerr |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparoascopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.

(56) References Cited

OTHER PUBLICATIONS

Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS

BACKGROUND

The present disclosure relates to surgical instruments. More particularly, the present disclosure relates to surgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps including a housing having a shaft attached thereto and an end effector assembly disposed at a distal end of the shaft. The end effector assembly includes first and second jaw members disposed in opposing relation relative to one another. One (or both) of the jaw members is moveable relative to the other between a spaced-apart position and an approximated position for grasping tissue therebetween. A cutting assembly is disposed within a cavity defined within the first jaw member. The cutting assembly includes a cutting member that is rotatably coupled to the first jaw member. The cutting member is rotatable with respect to the first jaw member about a longitudinal axis thereof to cut tissue disposed between the jaw members.

In one embodiment, one (or both) of the jaw members includes an electrically conductive tissue sealing surface disposed on an opposed surface thereof. Each sealing surface(s) may be adapted to connect to a source of electrosurgical energy for conducting energy through tissue disposed between the jaw members.

In another embodiment, the cutting assembly includes a cutting member positioned within the first jaw member and extending longitudinally therealong. The cutting member is configured to rotate about a rod, or bar disposed therethrough to cut tissue disposed between the jaw members.

In another embodiment, the cutting member includes a textured surface disposed on an outer peripheral surface thereof. The textured surface is configured to enhance tissue separation. Further, the outer peripheral surface may be configured to frictionally engaged tissue during rotation thereof to thermally enhance tissue separation.

In still another embodiment, the cutting member includes one or more textured barbs positioned on the outer periphery thereof that are configured to engage tissue during rotation hereof to enhance tissue separation.

In yet another embodiment, the cutting member defines a circular front cross-sectional configuration.

In still another embodiment, one or more drive components are disposed within the jaw member and are coupled to the cutting member. The drive component(s) is configured to electrically or electro-mechanically drive rotation of the cutting member with respect to the jaw member.

The present disclosure also relates to an end effector assembly for use with a forceps. The end effector assembly includes first and second jaw members disposed in opposed relation relative to one another. One (or both) of the jaw members is moveable with respect to the other between an open position and an approximated position for grasping tissue therebetween. An elongated cutting member is positioned within a cavity defined within the first jaw member and extends longitudinally therealong. The elongated cutting member is rotatably coupled to the first jaw member and is rotatable with respect to the first jaw member about a longitudinal axis thereof. The elongated cutting member may be rotated with respect to the first jaw member to cut tissue disposed between the jaw members. More specifically, the cutting member may be configured to frictionally cut tissue disposed between the jaw members upon rotation of the cutting member with respect to the first jaw member.

As in the previous embodiment, the elongated cutting member may define a circular front cross-sectional configuration.

In still another embodiment, the cutting member includes a textured surface disposed on the outer periphery thereof configured to enhance tissue separation.

In another embodiment, the cutting member includes one or more textured barbs positioned on the outer periphery thereof that are configured to engage tissue during rotation thereof to enhance tissue separation.

In yet another embodiment, one (or both) of the jaw members includes an electrically conductive tissue sealing surface disposed on an opposed surface thereof. Each sealing surface(s) may be adapted to connect to a source of electrosurgical energy for conducting energy through tissue disposed between the jaw members.

In still another embodiment, a drive component (or drive components) disposed within the first jaw member is configured to electrically or electro-mechanically drive rotation of the elongated cutting member with respect to the first jaw member.

BRIEF DESCRIPTION OF THE DRAWINGS

Various embodiments of the presently disclosed forceps are described herein with reference to the drawings, wherein.

DETAILED DESCRIPTION

Figure 1:
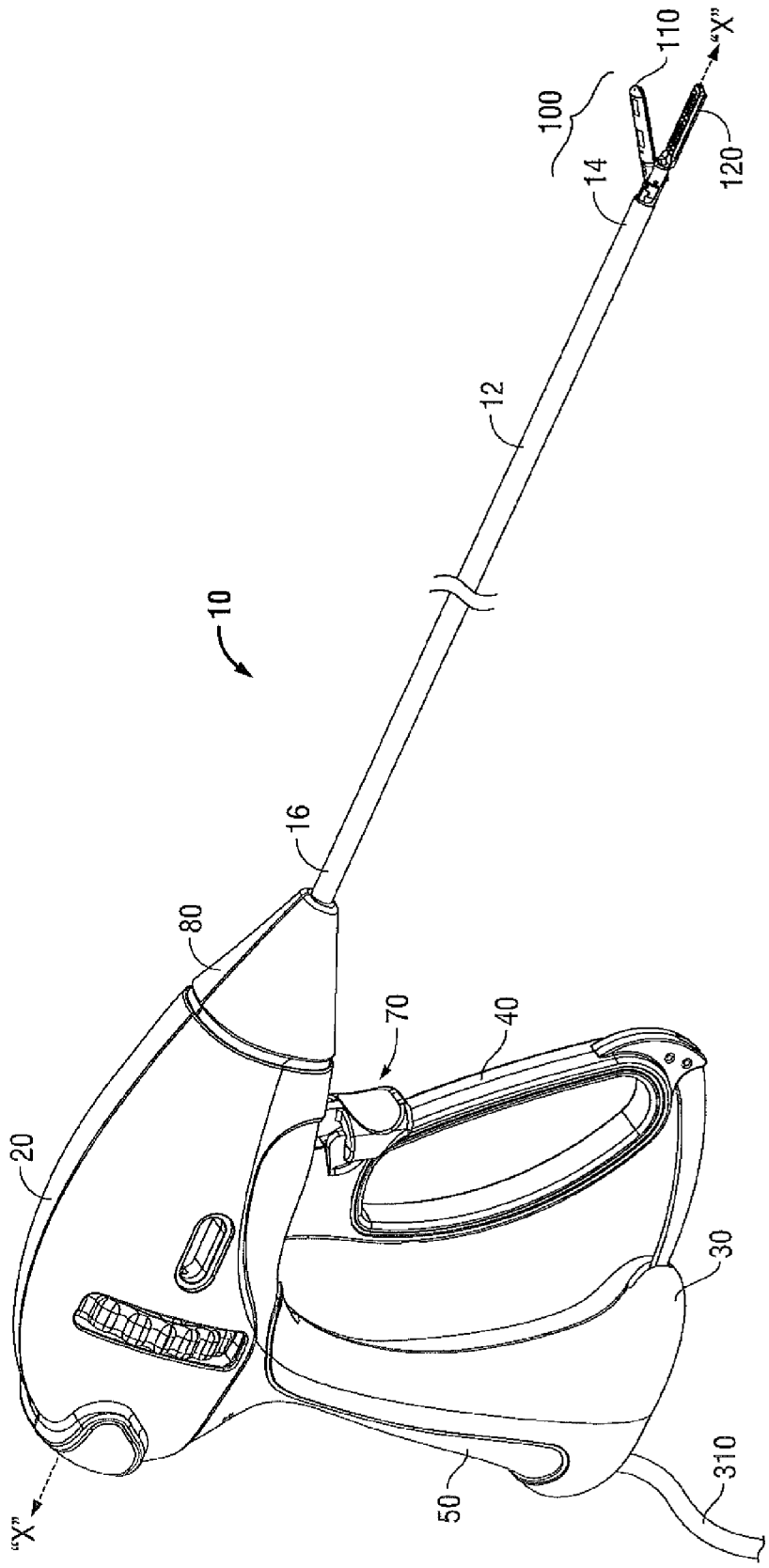
FIG. 1 is a perspective view of a forceps including an end effector assembly in accordance with an embodiment of the present disclosure.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, forceps 10 is one example of an instrument for use in accordance with the present disclosure. Forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Housing 20 includes two halves that house the internal working components of forceps 10.

End effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 (FIG. 2) relative to jaw member 120. However, either, or both jaw members 110, 120 may be moveable with respect to the other.

Forceps 10 also includes an electrosurgical cable 310 that connects forceps 10 to a generator (not shown). Cable 310 has sufficient length to extend through shaft 12 in order to provide electrical energy to at least one of jaw members 110 and 120 of end effector assembly 100. Alternatively, forceps 10 may be configured as a battery powered instrument.

With continued reference to FIG. 1, handle assembly 30 includes a fixed handle 50 and a moveable handle 40. Fixed handle 50 is integrally associated with housing 20 and moveable handle 40 is moveable relative to fixed handle 50. Moveable handle 40 of handle assembly 30 is ultimately connected to a drive assembly (not shown) that, together, mechanically cooperate to impart movement of jaw members 110 and 120 between an open, or spaced-apart position and a closed, or approximated position.

Rotating assembly 80 is integrally associated with housing 20 and is rotatable in either direction about a longitudinal axis "X-X" to rotate jaw members 110, 120 with respect to housing 20 about longitudinal axis "X-X."

Figure 2A:
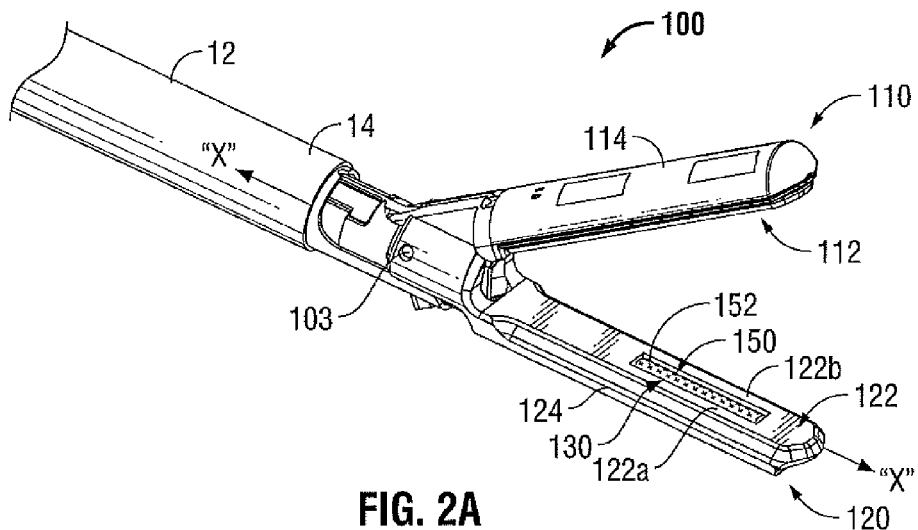
FIG. 2A is an enlarged, perspective view of the end effector assembly of FIG. 1.
Figure 2B:
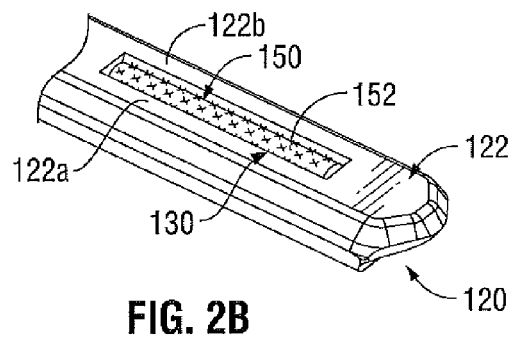
FIG. 2B is a greatly-enlarged perspective view of the area of detail shown in FIG. 2A.

Referring now to FIGS. 2A-2B, each jaw member 110, 120 of end effector assembly 100 includes an electrically conductive tissue sealing surface 112, 122, respectively, disposed on an opposed surface thereof and a respective outer jaw housing 114, 124. Jaw member 120 includes a channel 130 defined therein and extending longitudinally therealong. Channel 130 bisects sealing surface 122 of jaw member 120, dividing sealing surface 122 into sealing surface sections 122a and 122b. Channel 130 extends along a substantial length of jaw member 120 and may be centered about a longitudinal axis "X-X" of jaw member 120. A cutting assembly 150 including a cutting member 152 is operably coupled to jaw member 120. Cutting member 152 is positioned within channel 130 and is rotatable with respect to jaw member 120 about longitudinal axis "X-X" of jaw member 120.

More specifically, and with reference to FIGS. 3A-5, cutting assembly 150 includes a cutting member 152 having a lumen 154 extending therethrough, a rotating bar 156 configured to fixedly engage cutting member 152 through lumen 154, and one or more drive components 158 that are coupled to rotating bar 156 to rotate rotating bar 156 with respect to jaw member 120, thereby rotating cutting member 152 with respect to jaw member 120. One or more lead wires 160 extend through shaft 12 (FIG. 1) and are coupled to drive component(s) 158 for providing power to electrically or electro-mechanically rotate cutting member 152 about longitudinal axis "X-X."

Figure 3B:
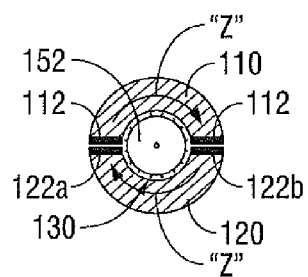
FIG. 3B is a front, cross-sectional view of the end effector assembly of FIG. 1.
Figure 3A:
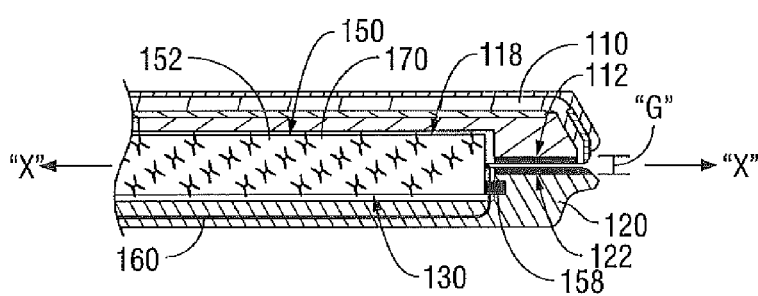
FIG. 3A is a side, cross-sectional view of the end effector assembly of FIG. 1.

As shown in FIGS. 3A-3B, and as mentioned above, cylindrical cutting member 152 is positioned within channel 130. Channel 130 is configured to seat cutting member 152 therein. More specifically, the length and width of channel 130 are greater than the length and width of cutting member 152 such that cutting member 152 may be positioned at least partially within channel 130. However, channel 130 may define a depth less than the diameter of cylindrical cutting member 152 such that at least a portion of cutting member 152 protrudes from channel 130, e.g., such that cutting member 152 extends from between sealing surface sections 122a, 122b and toward jaw member 110 when cutting member 152 is positioned within channel 130.

As best shown in FIG. 3A, jaw member 110 may include a complementary recessed portion, or channel 118 defined therein and configured to accommodate cutting member 152 upon approximation of jaw members 110, 120. Thus, when jaw members 110, 120 are moved to the approximated position, the portion of cutting member 152 protruding from channel 130 is positioned within channel 118, permitting jaw members 110, 120 to move to a fully approximated position. Alternatively, cutting member 152 and channel 130 may be configured such that cutting member 152 protrudes only slightly from channel 130 a distance smaller than the gap distance "G" between jaw members 110, 120 when jaw member 110, 120 are in the approximated position. In such an embodiment, a recess or channel need not be defined within jaw member 110 to permit full approximation of jaw members 110, 120. In either embodiment, upon approximation of jaw member 110, 120, cutting member 152 is positioned adjacent, but not in contact with sealing surface 112 of jaw member 110.

Figure 4:
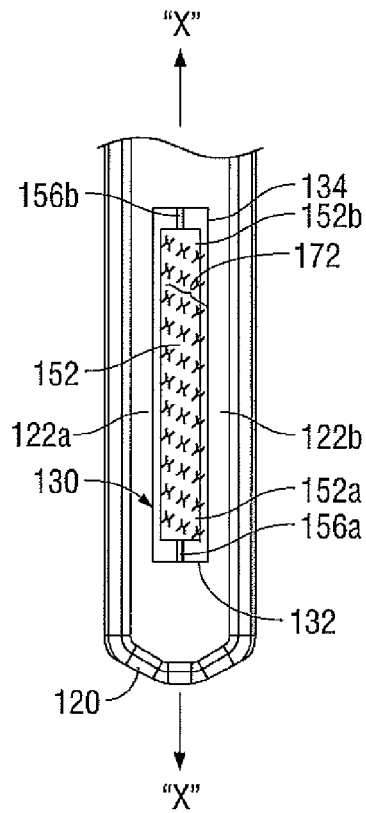
FIG. 4 is a top view of the end effector assembly of FIG. 1 wherein a top jaw member has been removed for viewing purposes.
Figure 5:
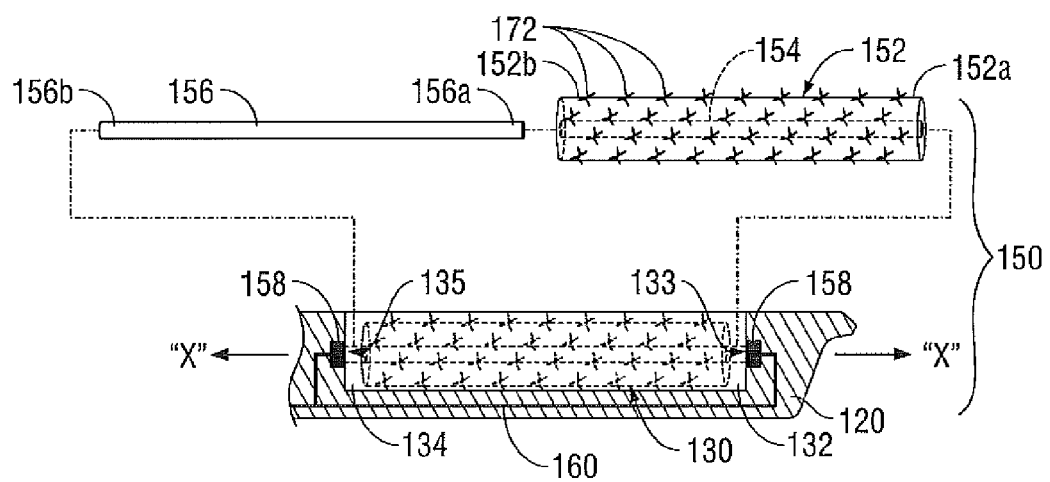
FIG. 5 is a side, cross-sectional view a bottom jaw member of the end effector assembly of FIG. 1 shown with parts separated.

With reference now to FIGS. 4-5, rotating bar 156 of cutting assembly 150 is fixedly engaged within lumen 154 of cutting member 152, e.g., via adhesion, welding, friction-fitting, etc. Rotating bar 156 defines a length greater than the length of cutting member 152 such that when rotating bar 156 is disposed through lumen 154, rotating bar 154 protrudes from both ends of lumen 154. More particularly, distal end 156a of rotating bar 156 protrudes from distal end 152a of cutting member 152 while proximal end 156b of rotating bar 156 protrudes from proximal end 152b of rotating bar 152. Alternatively, instead of rotating bar 156 being operably disposed through lumen 154 of cutting member 152 and protruding therefrom, rotating bar 156 may include two disconnected ends, a distal end 156a that is fixedly-engaged to distal end 152a of cutting member 152 and a proximal end 156b that is fixedly-engaged to proximal end 152b of cutting member 152. In such an embodiment, cutting member 152 may be solid, i.e., cutting member 152 need not have a lumen defined therethrough. Further, rotating bar 156 and cutting member 152 may be engaged via any other suitable mechanism wherein rotating bar 156 is fixedly-engaged to cutting member 152 and such that distal and proximal ends 156a, 156b, respectively, of rotating bar 156 protrude from respective distal and proximal ends 152a, 152b of cutting member 152.

With continued reference to FIGS. 4-5, a distal end 132 of channel 130 includes an aperture 133 defined therethrough. Aperture 133 is configured to receive distal end 156a of rotating bar 156 therein. Similarly, a proximal end 134 of channel 130 includes an aperture 135 defined therethrough and configured to receive proximal end 156b of rotating bar 156. During assembly, as best shown in FIG. 5, rotating bar 156 is engaged within lumen 154 of cutting member 152 and distal end 156a of rotating bar 156 is inserted through aperture 133 at distal end 132 of channel 130 while proximal end 156b of rotating bar 156 is inserted through aperture 135 at proximal end 134 of channel 130 to securely suspend cutting member 130 within channel 130. Apertures 133, 135, may be aligned with longitudinal axis "X-X" of jaw member 120 such that, when cutting member 152 is engaged within jaw member 120, cutting member 152 is centered with respect to longitudinal axis "X-X." Apertures 133, 135 are dimensioned to permit rotation of rotating bar 156 when rotating bar 156 is disposed therethrough.

A drive component 158 (or drive components 158) is disposed within jaw member 120 at one (or both) end 132 and/or 134 of channel 130. As mentioned above, distal and/or proximal ends 156a, 156b, respectively, of rotating bar 156 extend through apertures 133, 135, respectively, and are coupled to drive component(s) 158. Drive component(s) 158 is configured to electrically or electromechanically drive rotating bar 156, thereby rotating cutting member 152 with respect to jaw member 120. Lead wires 160 provide power to drive component(s) 158 and, thus, activate and/or deactivate drive component(s) 158. More specifically, lead wires 160 extend from drive component(s) 158, through shaft 12 (FIG. 1), and ultimately connect to an energy source, e.g., a battery (not shown) disposed within handle assembly 20 or a cable, e.g., cable 310, which is connected to an external source of energy, e.g., a generator (not shown).

Further, another of lead wires 160 may be coupled to an actuator, or trigger, e.g., trigger 70 (FIG. 1) for activating drive component(s) 158. In other words, when a user depresses trigger 70 (FIG. 1), lead wires 160 communicate energy to drive component(s) 158, activating drive component(s) 158 to, in turn, rotate cutting member 152 about longitudinal axis "X-X" of jaw member 120. As can be appreciated, when trigger 70 is released, energy is no longer supplied to drive component(s) 158 and, thus, drive component(s) 158 is deactivated, no longer driving the rotation of cutting member 152.

Alternatively, any other suitable rotatable cutting assembly 150 positionable within one (or both) of jaw members 110, 120 may be provided for rotating cutting member 152 with respect to jaw member 120.

Referring once again to FIGS. 3A-5, elongated cylindrical cutting member 152 may include a plurality of textured elements 172 disposed on an outer peripheral, or external surface 170 thereof. Textured elements 172 may be sharp barbs 172 positioned helically about cutting member 152, as shown in FIGS. 3A-5. However, textured elements 172 may alternatively be raised, recessed, or rough textured features defined on external surface 170 of cutting member 152. Further, textured elements 172 may be positioned in any suitable configuration on external surface 170 of cutting member 152. As will be described in greater detail below, textured elements 172 facilitate cutting of tissue disposed between jaw members 110, 120 upon rotation of cutting member 152 with respect to tissue.

The operation of forceps 10 will now be described with reference to FIGS. 1-5. Forceps 10 may be adapted for use in endoscopic procedures as well as in open surgical procedures. The configuration of forceps 10 is particularly advantageous for use in laparoscopic or endoscopic procedures due to the relatively small-diametered, elongated dimensions of shaft 12 and end effector assembly 100. More particularly, since cutting assembly 150 is completely disposed within jaw member 120 of end effector assembly 100, shaft 12 need not be configured to house additional components therein, e.g., a cutting mechanism. Eliminating the cutting mechanism or drive rods associated therewith from shaft 12 allows shaft 12 to define a reduced diameter. Further, positioning the cutting assembly 150 completely within jaw member 120 allows end effector assembly 100 to be rotated with respect to housing 20, e.g., via rotating the rotating assembly 80 (FIG. 1), without requiring repositioning or articulating of cutting assembly 150 with respect to jaw members 110, 120. Accordingly, forceps 10, having a reduced diameter and simplified maneuverability, may be inserted through relatively smaller incisions in tissue, allowing for quicker recovery time and reduced patient discomfort.

In use, as shown in FIG. 2, forceps 10 is initially positioned such that tissue to be sealed and/or cut is disposed between jaw members 110, 120, in the spaced-apart, or open position. As mentioned above, end effector assembly 100 may be rotated about longitudinal axis "X-X" to position jaw members 110, 120 about tissue. Next, moveable handle 40 (FIG. 1) is translated, i.e., squeezed, toward fixed handle 50 to move jaw members 110, 120 from the spaced-apart position to the approximated position wherein tissue is grasped between sealing surfaces 112, 122 of respective jaw members 110, 120. At this point, cutting member 152 of cutting assembly 150 remains un-actuated, or stationary with respect to jaw member 120. Although cutting member 152 may include exposed textured elements, e.g., barbs 172, tissue grasped between jaw members 110, 120 remains substantially undisturbed since cutting member 152 remains stationary with respect to tissue grasped between jaw members 110, 120. Electrosurgical energy may be supplied to sealing surfaces 112 and/or 122 for sealing tissue disposed therebetween. Accordingly, a tissue seal may be effected substantially along a width of sealing surfaces 112, 122 of jaw members 110, 120, respectively.

With tissue grasped between sealing surfaces 112, 122, e.g., after tissue sealing is complete, cutting assembly 150 may be activated to cut tissue, e.g., along the tissue seal. More specifically, trigger 70 (FIG. 1) may be depressed, or actuated to communicate energy through lead wires 160 to activate drive component(s) 158. When activated, the electrical or electromechanical drive component(s) 158, as mentioned above, drives the rotation of rotating bar 156 and, thus, cutting member 152, with respect to jaw member 120 about longitudinal axis "X-X" (as shown by arrows "Z" in FIG. 3B). Since tissue is clamped between jaw members 110, 120 cutting member 152 is also rotated with respect to tissue.

As cutting member 152 is rotated with respect to tissue, friction is created at the interface between external surface 170 of cutting member 152 and tissue, as external surface 170 is rotated relative to tissue. Drive component(s) 158 may be configured to rotate cutting member 152 at a sufficient rate so as to produce enough friction to create a cutting effect. Thus, when cutting member 152 is rotated at a sufficient rate, cutting member 152 frictionally dissects the previously sealed tissue disposed between jaw members 110, 120. Trigger 70 (FIG. 1) may be selectively depressible to increase and/or decrease the rotational speed of cutting member 152. As can be appreciated, the rotational speed required to sever a particular portion of tissue grasped between jaw members 110, 120 may vary, depending at least on the size and composition of tissue. Thus, selectively depressing trigger 70 allows a user to provide enough rotational speed to dissect through the particular size and/or composition of tissue disposed between jaw members 110, 120.

Textured elements 172, e.g., barbs 172, disposed on external surface 170 of cutting member 152 also facilitate cutting of tissue. More specifically, roughly textured elements increase the friction as cutting member 152 is rotated with respect to tissue to facilitate cutting, while sharp textured element cut through tissue as cutting element 152 is rotated with respect to tissue. Thus, textured elements 172 may reduce the rotational speed required to sever a particular portion of tissue and/or may reduce the time required to dissect through a particular portion of tissue.

Cutting assembly 150 may also include a locking mechanism (not shown) for inhibiting rotation of cutting member 152 with respect to jaw member 120 when jaw members 110, 120 are disposed in the spaced apart position. Such a feature would help prevent inadvertent cutting and/or injury due to accidental actuation of cutting assembly 150. The locking mechanism (not shown) may be automatic, inhibiting cutting assembly 150 from being activated while jaw members 110, 120 are in the spaced apart position, or may be selectively controlled such that cutting assembly 150 is biased toward a locked position when jaw members 110, 120 are in the spaced apart position. A selectively controlled locking mechanism (not shown) may permit actuation of cutting assembly 150 to dissect tissue when jaw members 110, 120 are in the spaced apart position upon depression of a safety lever, or switch (not shown).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A forceps, comprising:
   a housing having a shaft attached thereto and an end effector assembly disposed at a distal end of the shaft, the end effector assembly including:
      first and second jaw members defining electrically-conductive surfaces disposed in opposed relation relative to one another, at least one of the jaw members being moveable with respect to the other between a spaced-apart position and an approximated position for grasping tissue between the electrically-conductive surfaces, the first jaw member defining a cavity extending through and surrounded by the electrically-conductive surface of the first jaw member, at least one of the electrically-conductive surfaces adapted to connect to a source of energy for conducting energy through tissue grasped between the electrically-conductive surfaces to treat tissue on either side of the cavity; and
      a cutting assembly including a cutting member disposed within the cavity and rotatably coupled to the first jaw member, the cutting member configured to rotate with respect to the first jaw member about a longitudinal axis thereof to cut tissue between treated portions of tissue.

2. The forceps according to claim 1, wherein the cutting member is positioned within the first jaw member and extends longitudinally therealong, the cutting member configured to rotate about a rod disposed therethrough to cut tissue disposed between the jaw members.

3. The forceps according to claim 1, wherein the cutting member includes a textured surface disposed on an outer peripheral surface thereof.

4. The forceps according to claim 3, wherein the cutting member includes a plurality of textured barbs positioned on the outer periphery thereof that are configured to engaged tissue during rotation thereof.

5. The forceps according to claim 1, wherein the cutting member defines a circular front cross-sectional configuration.

6. The forceps according to claim 1, wherein at least one drive component is disposed within the first jaw member, the at least one drive component configured for one of electrically and electromechanically driving rotation of the cutting member with respect to the first jaw member.

7. An end effector assembly for use with a forceps, the end effector assembly comprising:
   first and second jaw members defining electrically-conductive surfaces disposed in opposed relation relative to one another, at least one of the jaw members being moveable with respect to the other between a spaced-apart position and an approximated position for grasping tissue between the electrically-conductive surfaces, the first jaw member defining a cavity extending through and surrounded by the electrically-conductive surface of the first jaw member, at least one of the electrically-conductive surfaces adapted to connect to a source of energy for conducting energy through tissue grasped between the electrically-conductive surfaces to treat tissue on either side of the cavity; and
   an elongated cutting member positioned within the cavity and extending longitudinally therealong, the elongated cutting member rotatably coupled to the first jaw member and rotatable with respect to a longitudinal axis of the first jaw member to cut tissue between treated portions of tissue.

8. The end effector assembly according to claim 7, wherein the cutting member defines a circular front cross-sectional configuration.

9. The forceps according to claim 7, wherein an outer peripheral surface of the cutting member is configured to frictionally engage tissue during rotation thereof.

10. The forceps according to claim 7, wherein the cutting member includes a plurality of textured barbs positioned on an outer peripheral surface thereof that are configured to engaged tissue during rotation thereof.

11. The end effector assembly according to claim 7, wherein, at least one drive component is disposed within the first jaw member, the at least one drive component configured for one of electrically and electromechanically driving the rotation of the elongated cutting member with respect to the first jaw member.

* * * * *